United States Patent [19]

Horrom

[11] 4,110,471

[45] * Aug. 29, 1978

[54] N-VINYLOXYETHYL-α-METHYL-β-PHENE-THYLAMINES AS ALCOHOL INTAKE SUPPRESSING AGENTS

[75] Inventor: Bruce Wayne Horrom, Waukegan, Ill.

[73] Assignee: Abbott Laboratories, North Chicago, Ill.

[ * ] Notice: The portion of the term of this patent subsequent to Dec. 21, 1993, has been disclaimed.

[21] Appl. No.: 721,614

[22] Filed: Sep. 8, 1976

[51] Int. Cl.² .................................. A61K 31/135
[52] U.S. Cl. ............................................ 424/330
[58] Field of Search ................................. 424/330

[56] References Cited

U.S. PATENT DOCUMENTS 3,998,971  12/1976  Horrom ................................ 424/330

Primary Examiner—Albert T. Meyers
Assistant Examiner—Daren M. Stephens
Attorney, Agent, or Firm—Robert L. Niblack; Gildo E. Fato

[57] ABSTRACT

N-vinyloxyethyl-α-methyl-β-phenethylamines represented by the formula

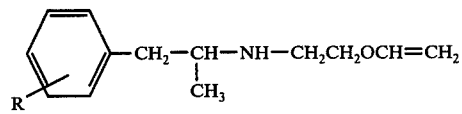

wherein R is H, halo or CF₃ and acid addition salts thereof have been found to be useful as alcohol intake suppressing agents.

3 Claims, No Drawings

N-VINYLOXYETHYL-α-METHYL-β-PHENE-THYLAMINES AS ALCOHOL INTAKE SUPPRESSING AGENTS

DETAILED DESCRIPTION OF THE INVENTION

This invention relates to novel phenethylamine derivatives, particularly N-vinyloxyethyl-α-methyl-β-phenethylamines as alcohol intake suppressing agents.

After cardiovascular disease, alcoholism is the biggest health problem in the United States; over nine million Americans are alcoholics. Concern for the problem of alcoholism may be represented by the fact that in 1975 approximately $350 million was allocated by Congress to the National Institute on Alcohol Abuse and Alcoholism for research and to publicize the dangers of alcoholism.

While many psychotherapeutic drugs have been used in the treatment of alcoholism, none have proven to be of any real value. These include: tranquilizers, antidepressants, anticonvulsants, vitamins, sedatives and biochemical interference agents like disulfuram.

Disulfuram (Antabuse) is the only drug listed as an anti-alcohol drug in the present marketing literature. This drug has been available for some time but has never been widely used because it is an aversive treatment with many side effects. In this context, a drug which would inhibit the intake of ethanol without aversive side effects would have greater patient acceptance and considerably more market potential.

The compounds of this invention are represented by the formula

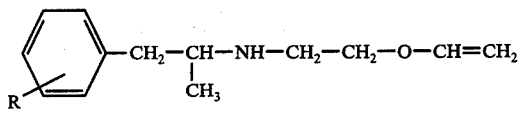

wherein R is hydrogen, halo or trifluoromethyl and acid addition salts thereof.

The term "halo" as used herein, includes chloro, fluoro, bromo and iodo.

The compounds of this invention are patented in my previously issued patent (U.S. Pat. No. 3,925,475 issued 12/9/75). The use of the compounds as diet depressants is disclosed in the same patent and is the subject of a copending Divisional application Ser. No. 611,951, filed 9/10/75.

The compounds are useful as alcohol intake suppressing agents when administered orally to mammals in dosages of from 5 to 40 mg/kg of body weight daily.

The preparation of the compounds of this invention is represented by the following reaction sequence:

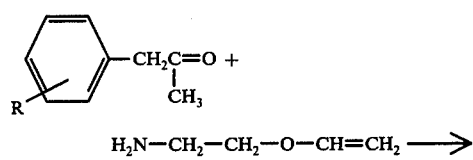

-continued

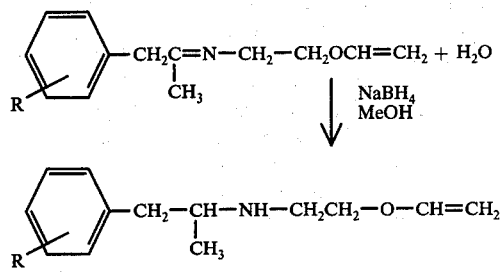

The following examples further illustrate the present invention:

ALCOHOL INTAKE STUDIES

A. Rats

METHODS: The procedure was adapted from Veale and Myers (Psychopharmacologia, 15, 361–72, 1969). Male Long-Evans rats were housed in individual cages and fed Purina Rat Chow ad libitum. Water and ethanol solutions (at concentrations determined by the animal's level of preference) were available from graduated drinking tubes 24 hours per day, seven days a week. Three of the graduated tubes (Richter tubes) were mounted on the front of each animal's cage. One of the tubes was filled with tap water, another with an ethanol solution, and the third was left empty and served as a position control. Every day the volume of ethanol and water was recorded; the tubes were refilled and positioned according to a random sequence for a three-choice situation.

RESULTS: Each animal served as its own control; the five days preceding a drug were used as the baseline. Preference was calculated for each animal by dividing the volume of ethanol consumed by the total volume of fluid consumed x 100. Average preference for six rats during drug administration was then compared to the baseline preference level. The results of a series of ten-day studies with a dose range of the inventive compounds and a single dose of disulfuram, p-chlorophenylalanine (p-CPA) and the suspending agent, tragacanth, are shown in FIG. 1. P-CPA was tested as a reference in addition to disulfuram because it has been reported to be an effective reducer of alcohol preference in rats (Veale and Myers, Int. J. Neuropharm., 9:317–326, 1970).

The mean values of alcohol, water and total fluid (in ml) consumed for control-baseline and drug period for each experiment are presented in the third through eighth columns of FIG. 1. All drug treatments tended to lower alcohol intake relative to controls and raise water intake. With the exception of p-CPA, the increase in water was insufficient to effect an increase in total fluid consumed. P-CPA produced a much greater increase in water intake than any of the other treatments shown.

The mean preference values for alcohol during control-baseline and drug for each experiment are presented in columns nine and ten. The greatest decrease in alcohol preference relative to control was produced by the inventive compounds at 40 mg/kg.

The tenth column (Percent of Control) presents the effect of drug on preference as percent of control preference. The control value is divided into the drug value x 100 to give a percent of control value. A percentage value of 70 means that the drug reduced preference by 30%. The inventive compounds reduced preference by 65.7% at 40 mg/kg, disulfuram at 200 mg/kg produced at 52.1% decrease, and p-CPA at 200 mg/kg produced a 35% reduction. It is clear from a study of FIG. 1 that the suspending vehicle, tragacanth (placebo) exerted no effect. The greatest effect was obviously produced by N-vinyloxy-ethyl-α-methyl-β-phenethylamine at 40 mg/kg, followed by 20 mg/kg, then disulfuram and then p-CPA. The 10 mg/kg dose of the inventive compound was replicated twice to ascertain the validity of its position in the dose-response curve.

In the course of treatment with p-CPA, animals lost weight and body hair and evidenced a discoloration of the urogenital region. These side effects were not observed with the inventive compounds or disulfuram.

Note, that every treatment lowered preference for alcohol, and the extent and effect was proportional to the size of the dose. This is a linear dose-response relationship obtained over the entire range of dosages studied. The potency of effect and the consistency of dose-response effect throughout the range of doses is superior to any compounds tested in the procedure to-date.

Five to seven days, over which the animal's choice pattern was fairly consistent, constituted the baseline used as the control. Test drugs were administered orally either once or twice a day for four consecutive days. Test compounds were suspended in tragacanth or carboxymethylcellulose (0.5%) and masked with a portion of fruit juice.

The apparatus was controlled by electromechanical programming equipment located in an adjacent room. Fifteen ml of a 30% ethanol (by volume) solution (one ethanol reinforecement) was made contingent on five presses (FR 5) of an orange toggle switch; fifteen ml of tap water (one water reinforcement) was contingent on FR 5 on the green toggle switch; delivery of a one-gram banana pellet (one food reinforcement) was contingent upon depressing the red toggle switch once every two minutes on the average (random interval, two minutes). Data were recorded on electromechanical counters and cumulative recorders. Data were also acquired by an 11/40 Digital equipment corporation computer.

RESULTS: The results of treatment with 2.5, 5, 10, and 20 mg/kg of the compound, 40 and 80 mg/kg b.i.d.

Figure 1

SUMMARY OF EFFECTS OF N-VINYLOXYETHYL-α-METHYL-β-CHLORO-PHENETHYLAMINE (COMPOUND), DISULFURAM AND p-CPA ON ALCOHOL PREFERENCE IN THE RAT ALCOHOL INTAKE TEST

|  |  | Mean Ml Fluid Consumed (N-6) |  |  |  |  |  | Alcohol Preference[1] |  | Alcohol Percent of Control[2] (Drug/Control) |
|---|---|---|---|---|---|---|---|---|---|---|
|  | Dose | Alcohol Soln. |  | Water |  | Total Liquid |  |  |  |  |
| Drug | mg/kg p.o. | Control | Drug | Control | Drug | Control | Drug | Control | Drug |  |
| Tragacanth |  | 61.3 | 54.2 | 2.5 | 2.1 | 63.8 | 56.3 | 95.3 | 94.6 | 99.2 |
| COMPOUND | 5 | 38.2 | 17.4 | 3.5 | 5.3 | 41.8 | 22.8 | 89.1 | 71.1 | 79.7 |
|  | 10 | 53.7 | 25.0 | 5.4 | 8.0 | 58.1 | 33.1 | 90.5 | 59.9 | 66.2 |
|  | 10 | 54.3 | 18.6 | 3.4 | 8.1 | 57.7 | 26.8 | 92.9 | 63.6 | 68.4 |
|  | 10 | 53.6 | 29.3 | 1.5 | 5.8 | 55.1 | 35.1 | 97.4 | 75.0 | 77.0 |
|  | 20 | 40.7 | 7.9 | 5.9 | 7.6 | 46.5 | 15.5 | 86.5 | 37.9 | 43.8 |
|  | 40 | 43.8 | 5.3 | 4.8 | 14.8 | 49.5 | 21.2 | 88.7 | 30.4 | 34.3 |
| Disulfuram | 200 | 41.8 | 16.0 | 5.0 | 19.6 | 46.8 | 35.6 | 87.9 | 42.1 | 47.9 |
| p-CPA | 200 | 57.6 | 39.6 | 3.0 | 25.3 | 60.6 | 64.9 | 95.1 | 60.3 | 63.4 |

[1]Alcohol Preference (calculated for each subject individually, then averaged, to prevent "weighting" of drug effect by subjects which consume larger volumes of liquid) =
$$\frac{\text{Ml Etoh Soln.}}{\text{Ml alcohol Soln.} + \text{Ml Water}} \times 100 \text{ (expressed as a percent of total liquid consumed).}$$
[2]Percent of control is the ratio of Drug preference to Control preference. A value of 70% means that the drug treatment decreased the preference value by 30%.

B. Baboon

METHODS: A 20 kg male baboon was given the option of food, water, or alcohol reinforcement on a 24-hour, seven-day a week basis. The number of each type of reinforcement and the absolute amounts consumed were recorded daily. Under baseline conditions the animal took 30-40 % of all reinforcement in ethanol. Its absolute ethanol dosage consumed was a highly stable 2.5 ml/kg/day. The aversive tasting ethanol solution was established as a reinforcer by a combination of methods: schedule-induced polydipsia; gradual incrementation of ethanol concentration; and the use of grapefruit juice as a taste-masking agent.

of p-CPA and the suspending agent alone are presented in FIG. 3. Each bar represents the effect that the drug had on ethanol preference. A value of 70% in this graph means that the control preference was decreased by 30%.

FIG. 2 summarizes the absolute number of food, water, and alcohol reinforcements taken during the control and drug periods. Ethanol preference was calculated by dividing the number of alcohol reinforcements by the total of ethanol, water, and food reinforcements. Note that treatment with the suspending agent (placebo) produced no significant change from control (FIG. 2).

Figure 2

SUMMARY OF EFFECTS OF N-VINYLOXYETHYL-α-METHYL-β-CHLOROPHENETHYL-AMINE (COMPOUND) AND p-CPA ON ALCOHOL PREFERENCE IN THE BABOON ALCOHOL INTAKE TEST

| Drug | Dose mg/kg p.o | Number of Reinforcements | | | | | | Alcohol | | | Water | | | Food | | |
|---|---|---|---|---|---|---|---|---|---|---|---|---|---|---|---|---|
| | | Alcohol Soln. | | Water | | Food | | Alcohol Preference[1] | | Percent of Control[4] | Water Preference[2] | | Percent of Control[4] | Food Preference[3] | | Percent of Control[4] |
| | | Control | Drug | Control | Drug | Control | Drug | Control | Drug | (Drug/Control) | Control | Drug | (Drug/Control) | Control | Drug | (Drug/Control) |
| Methocel | 20 cc/kg | 334 | 265 | 139 | 147 | 240 | 225 | 46.9 | 41.6 | 88.6 | 19.5 | 23.1 | 118.5 | 33.7 | 35.3 | 104.8 |
| | 20 cc/kg | 242 | 309 | 204 | 184 | 135 | 121 | 41.7 | 50.3 | 120.6 | 35.1 | 30.0 | 85.5 | 23.3 | 19.7 | 84.5 |
| COMPOUND | 2.5 | 147 | 140 | 232 | 185 | 214 | 221 | 24.8 | 25.6 | 103.4 | 39.1 | 38.4 | 86.7 | 36.1 | 40.5 | 112.2 |
| | 5 | 191 | 86 | 244 | 160 | 228 | 171 | 28.8 | 20.6 | 71.5 | 36.8 | 38.4 | 104.3 | 34.4 | 41.0 | 119.2 |
| | 10 | 193 | 118 | 162 | 128 | 191 | 178 | 35.3 | 27.8 | 78.8 | 29.7 | 28.5 | 99.3 | 35.0 | 41.0 | 117.2 |
| | 10 | 176 | 135 | 261 | 153 | 226 | 161 | 26.5 | 30.1 | 113.5 | 39.4 | 34.1 | 86.5 | 34.1 | 35.9 | 105.2 |
| | 20 | 325 | 196 | 144 | 222 | 248 | 43.7 | 35.6 | 20.7 | 26.4 | 23.6 | 89.6 | 29.9 | 40.7 | 136.2 | |
| p-CPA | 40 B.I.D. | 284 | 149 | 256 | 326 | 228 | 245 | 37.0 | 20.7 | 55.9 | 33.3 | 45.3 | 136.0 | 29.7 | 34.0 | 114.5 |
| | 40 B.I.D. | 278 | 216 | 190 | 172 | 202 | 195 | 41.5 | 37.0 | 89.2 | 28.4 | 29.5 | 103.9 | 30.1 | 33.4 | 111.0 |
| | 80 B.I.D. | 366 | 263 | 147 | 193 | 233 | 179 | 49.0 | 41.4 | 84.4 | 19.7 | 30.4 | 154.3 | 31.2 | 28.2 | 90.4 |

[1] Alcohol Preference = $\dfrac{\text{EtOH Reinforcements}}{\text{EtOH} + \text{H}_2\text{O} + \text{Food Reinforcements}} \times 100$

[2] Water Preference = $\dfrac{\text{Water Reinforcements}}{\text{EtOH} + \text{H}_2\text{O} + \text{Food Reinforcements}} \times 100$

[3] Food Preference = $\dfrac{\text{Food Reinforcements}}{\text{EtOH} + \text{H}_2\text{O} + \text{Food Reinforcements}} \times 100$

[4] Percent of control is the ratio of Drug preference to Control preference. A value of 70% means that the drug treatment decreased the preference value by 30%.

FIG. 2 also presents water and food preference for Control and Drug. Water preference is calculated by dividing the number of water reinforcements by the total number of reinforcements. Similarly food preference is equal to food reinforcements divided by total reinforcements. The third column under Alcohol, Food, and Water gives the drug effect on preference as percent of control (Drug preference/Control preference). An entry of 80.0 represents a 20 percent decrease in preference.

FIG. 2 shows that both N-Vinyloxyethyl-α-Methyl-β-phenethylamine and p-CPA decreased alcohol preference. Water preference was increased by as much as 36% by p-CPA but tended to be affected little by the compound. Food preference was slightly affected or unaffected by the compound of p-CPA.

I claim:

1. A method of suppressing alcohol intake in mammals comprising administering a therapeutically effective amount of a compound of the formula

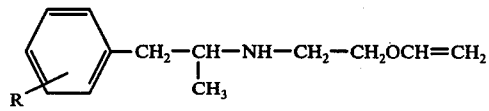

where R is H, halo, or $CF_3$ and acid addition salts thereof to said mammal.

2. The method of claim 1 which comprises administering N-vinyloxyethyl-α-methyl-β-chlorophenethylamine hydrochloride.

3. The method of claim 2 wherein said compound is administered orally in a dosage of from 5 to 40 mg/kg of body weight.